US00PP35382P2

(12) United States Plant Patent
Hansen

(10) Patent No.: US PP35,382 P2
(45) Date of Patent: Sep. 12, 2023

(54) **X *MANGAVE* PLANT NAMED 'PERMANENT WAVE'**

(50) Latin Name: **x *Mangave times* x *Agave* hybrid**
Varietal Denomination: Permanent Wave

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/803,938

(22) Filed: Jan. 26, 2023

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique X *Mangave* plant named 'Permanent Wave' is characterized by a compact mounded habit of ovate to deltoid-ovate leaves with dense, overlapping, intensely-glaucous, light-gray color. The new plant has large marginal teeth ending in a small, sharp, firm tooth and a large firm sharp apical mucro. The foliage frequently has depression images of the teeth left in the tops and bottoms of the leaves. The new plant has a moderate growth rate. The new plant is suitable as a potted houseplant plant, as a container plant for the patio or garden, and for the garden or planted in the landscape.

1 Drawing Sheet

Botanical classification: x *Mangave* times x *Agave* hybrid.
Variety denomination: 'Permanent Wave'.

STATEMENT REGARDING PRIOR DISCLOSURES UNDER 37 CFR 1.77(b)(6)

The first non-enabling public disclosure of x *Mangave* 'Permanent Wave' was on Feb. 1, 2022, with a brief description and photo on a website operated by Walters Gardens, Inc. This was followed by a brief description and photograph in the "Walters Gardens 2022-2023 Catalog" which was first distributed on Jun. 8, 2022. The first disclosure of the claimed plant, in the form of a sale, is planned to be made by Walters Gardens, Inc. on Feb. 15, 2022, to Plant Delights Nursery, Inc. All plants and information on 'Permanent Wave' have been provided to Walters Gardens, Inc. by the inventor. No plants of x *Mangave* 'Permanent Wave' have been sold or offered for sale, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct x *Mangave* plant, x *Mangave* 'Permanent Wave' hybridized on Nov. 23, 2015, by the inventor at a wholesale perennial nursery in Zeeland, Mich., USA as a cross between the proprietary unreleased hybrid known only by the breeder code x *Mangave* 12-11-1 (not patented) as the female or seed parent, and a proprietary selection of *Agave ovatifolia* (not patented) as the male or pollen parent. Through trials at the same nursery, the plant was referred to by the breeder code 16-56-2. The new plant has been successfully asexually propagated by shoot tip tissue culture in 2020 at the same nursery in Zeeland, Mich. These asexual propagation systems have been found to produce stable and identical plants that maintain all the unique characteristics of the original plant in successive generations.

BRIEF SUMMARY OF THE INVENTION x *Mangave* 'Permanent Wave' differs from its parents as well as all other *Manfreda, Agave,* and x *Mangave* known to the applicant. The most similar known x *Mangave* cultivars known to the inventor are: 'Lavender Lady' U.S. Plant Pat. No. 29,194, 'Whale Tale' U.S. Plant Pat. No. 31,060, 'Falling Waters' U.S. Plant Pat. No. 30,650, 'Silver Fox' U.S. Plant Pat. No. 29,642, *Agave* 'Frosty Blue' (not patented), and *Agave colorata.*

The female parent has shorter, more wavy, and more glaucous foliage that is more folded along the midrib. The male parent, selection of *Agave ovatifolia*, is slower growing, and has a larger habit with flatter leaves.

'Lavender Lady' has shorter, more ovate, and flatter leaves that are more upright in habit, with smaller marginal teeth and a purplish cast. 'Whale Tale' has more leaves per plant, narrower, more arching, and more folded foliage, with smaller marginal teeth and faint burgundy spotting. 'Falling Waters' has longer, narrower, more arching foliage that has less glaucous covering with purple spotting. 'Silver Fox' is smaller in habit with leaves that are lanceolate with purple-lavender spots. *Agave* 'Frosty Blue' has shorter, broader, and flatter foliage that is more bluish than bluish-gray, the marginal teeth are larger and more burgundy-colored, and the growth rate is much slower.

The new plant, 'Permanent Wave', is unique from all *Agave*, X *Mangave*, and *Manfreda* known to the inventor by the following combined traits:

1. Compact mounded habit;
2. Leaves ovate to ovate-deltoid, dense, overlapping, intensely-glaucous, light bluish-gray;

3. Foliage with large marginal teeth having a small sharp tooth and a large, firm, sharp, apical mucro;
4. Moderate growth rate.

BRIEF DESCRIPTION OF THE DRAWING

The photograph of the new plant demonstrates the overall appearance of the new plant including the unique traits grown with supplemental water and fertilizer as needed. The colors are as accurate as reasonably possible with color reproductions. Ambient light spectrum, temperature, source and direction may cause the appearance of minor variation in color.

The FIGURE shows a side angle view of a three-year-old plant grown in a container.

DETAILED BOTANICAL DESCRIPTION

The following descriptions and color references are based on the 2015 edition of The Royal Horticultural Society Colour Chart except where common dictionary terms are used. The new plant, X *Mangave* 'Permanent Wave', has not been observed under all possible environments. The phenotype may vary slightly with different environmental conditions, such as temperature, light, fertility, moisture, and maturity levels, but without any change in the genotype. The following observations and size descriptions are of a three-year-old plant in a commercial wholesale greenhouse and in a full-sun trial garden in Zeeland, Mich. with supplemental water and fertilizer as needed.

Botanical classification: x *Mangave* hybrid (*Manfreda* x *Agave*);

Parentage: The female or seed parent is the proprietary hybrid 12-11-1 comprising *Manfreda maculosa* and *Agave colorata*, and the male or pollen parent is *Agave ovatifolia;*

Propagation: Division and sterile plant tissue culture;

Time to initiate roots from tissue culture: About 28 days;

Growth rate: Moderate;

Crop time: About 20 to 26 weeks to finish during lengthening spring days from an established 25 mm tissue culture plug to a 65 mm diameter container;

Rooting habit: Fleshy, lightly branching, with roots up to 20 cm long;

Root color: Nearest RHS 158C depending on soil type;

Plant shape and habit: Succulent herbaceous perennial with basal rosettes of up to about 26 fleshy leaves radially emerging and arching from central rhizome, producing a symmetrical, low, rounded mound;

Plant size: Foliage height about 28 cm tall from soil line to the top of the foliage and 76 cm wide near soil level;

Foliage description: Ovate to ovate-deltoid; simple; sarcous; fibrous; glabrous; smooth and intensely-glaucous adaxial and abaxial; margins dentate with teeth 12 mm apart in the middle and 34 mm apart distally; tooth size to 11 mm long and 10 mm wide with the distal 3 mm hard, firm, and sharp; apex acute with sharp firm mucro; base truncate, sessile, clasping; slightly sinuate; distally slightly arching with maturity; teeth frequently leaving depression image in leaves above and below;

Leaf size: To about 35 cm long, about 16 cm wide about one-third away from base, and 1 cm thick at base; typically bi-laterally symmetrical; without spots;

Foliage fragrance: None observed;

Leaf color:

*Adaxial young and mature*.—Blend between RHS 189A, RHS 189B, and RHS N138C.

*Abaxial young and mature*.—Blend between RHS N138A, N138C, and RHS 189B.

*Marginal teeth*.—Mature adaxial and abaxial between RHS 200A and RHS 200B; adaxial and abaxial on younger foliage between RHS 166A and RHS 183A.

Mucro: Semi-flexible; sharp; straight, about 18 mm long and 3 mm across in the basal 5 mm;

Mucro color: On young leaves between RHS 166A and RHS 183A maturing to nearest RHS 200B;

Petiole: Sessile;

Veins: Parallel; not distinct;

Flower description: Not yet observed;

Fruit: Not yet observed;

Seed: Not yet observed;

Disease resistance: x *Mangave* 'Permanent Wave' has not been observed to be resistant to diseases common to other x *Mangave* beyond that which is normal for *Agave* or *Manfreda*. The plant is xeromorphic and survives well with minimal water once established. Hardiness at least from USDA zone 7b to 11. Full extent of winter hardiness has not been tested.

I claim:

1. A new and distinct cultivar of ornamental X *Mangave* plant named 'Permanent Wave' as herein described and illustrated.

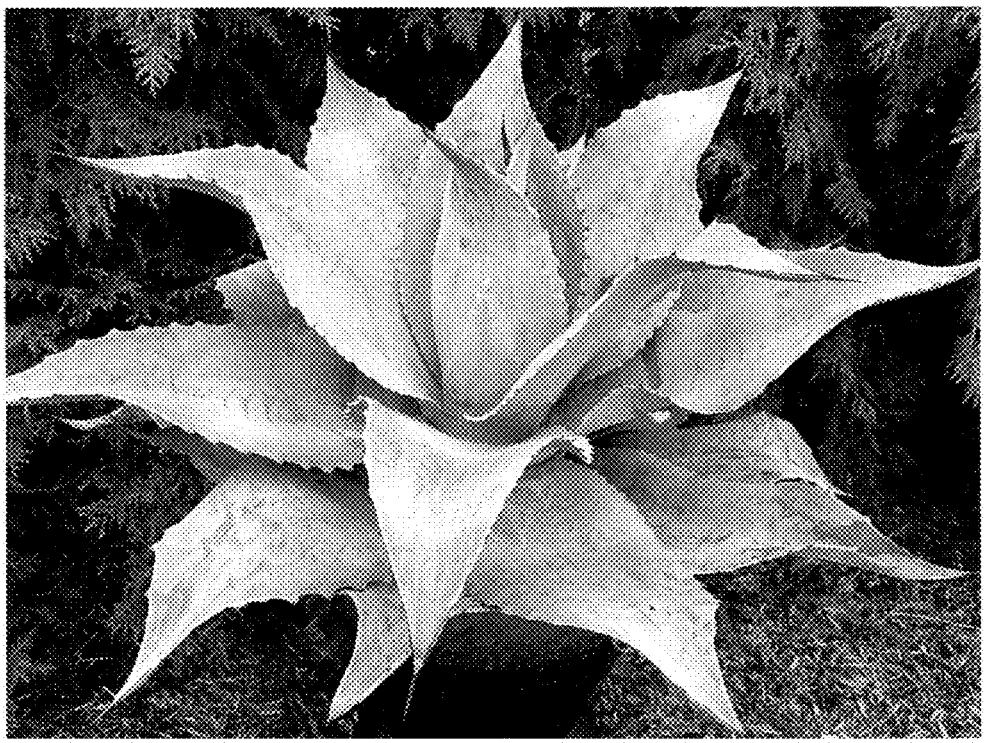

* * * * *